US00PP10434P

United States Patent [19]

Cain

[11] Patent Number: Plant 10,434

[45] Date of Patent: Jun. 9, 1998

[54] GRAPEVINE CV. 'SUGRATHIRTEEN'

[75] Inventor: David W. Cain, Bakersfield, Calif.

[73] Assignee: Sun World, Inc., Bakersfield, Calif.

[21] Appl. No.: 694,185

[22] Filed: Aug. 8, 1996

[51] Int. Cl.[6] ..... A01H 5/00

[52] U.S. Cl. ..... Plt./47.1

[58] Field of Search ..... Plt./47.1

[56] References Cited

U.S. PATENT DOCUMENTS

P.P. 7,377 11/1990 Antcliff ..... Plt./47.1

P.P. 9,039 1/1995 Larson ..... Plt./47.1

P.P. 9,040 1/1995 Larson ..... Plt./47.1

*Primary Examiner*—James R. Feyrer

*Assistant Examiner*—Kent L. Bell

*Attorney, Agent, or Firm*—Knobbe, Martens, Olson & Bear, LLP

[57] ABSTRACT

A new and distinct grapevine variety characterized by its high productivity and its firm, low acid, early ripening, naturally large, elongated black fruit, which does not require exogenous applications of gibberellic acid to obtain commercially acceptable berry size.

1 Drawing Sheet

BACKGROUND AND SUMMARY OF THE INVENTION

This invention relates to the discovery and asexual propagation of a new variety of grapevine, *Vitus vinifera* cv. 'Sugrathirteen.' The new variety was first hybridized in May 1990 by David W. Cain in Wasco, Kern County, Calif., the variety being originated by controlled hybridization and subsequent ovule culture. In particular, the 'Sugrathirteen' variety was created by hybridization of two "seedless" grape varieties possessing small, abortive, vestigial ovules. From an initial population of 1363 hybrid ovules, embryo rescue methods were used to product a population of 172 plants from which the present variety was selected. The new variety is characterized by producing firm, low acid, early ripening, naturally large black, elongated berries that do not require exogenous applications of gibberellic acid to obtain commercially acceptable berry size.

The variety has as its seed parent, an unnamed, unpatented grapevine seedling designated as seedling 17-138, which itself resulted from a cross of 'Italia'×'Sugraone'. Its polen parent is a grapevine seedling named 'Fantasy Seedless' (an unpatented variety). The parent varieties were first crossed in May 1990, with the date of first flowering being May 1992. The new 'Sugrathirteen' variety was first asexually propagated by David W. Cain in Dec. 1992, in Wasco, Kern County, Calif., using hardwood cuttings.

The new grapevine variety cv. 'Sugrathirteen' most nearly resembles its pollen parent variety, 'Fantasy Seedless'. It can be distinguished from Fantasy by its production of fruits which ripen approximately one month earlier, and which have firmer, slightly smaller, more variable, less elongate berries with better eating quality and better attachment than Fantasy. The grapevine is less vigorous but more productive than Fantasy. It also differs from Fantasy by having less distinct red fall foliage color and retaining its green foliage later in the fall than does the Fantasy variety. The 'Sugrathirteen' variety differs from its seed parent, seedling 17-138, by having elongated, black berries, rather than oval, white berries, and by having smaller vestigial seeds.

Furthermore, 'Sugrathirteen' can be distinguished from the presently available commercial cultivar, 'Beauty Seedless' (an unpatented variety), by having larger, firmer, and slightly more variable berries with much better berry attachment and eating quality. The 'Sugrathirteen' berries also exhibit a higher sugar-to-acid ratio than the berries of 'Beauty Seedless'. The new 'Sugrathirteen' variety has a lower chilling requirement (hours of temperatures between 32° F. and 45° F. needed to satisfy the winter dormancy requirement) than 'Perlette', 'Thompson Seedless' and Fantasy cultivars, and exhibits more uniform bud break than those varieties when grown in Mecca, Calif. (Coachella Valley in Riverside County, an early production region characterized by having short, warm winters where typically between 150 and 300 chilling hours are accumulated compared to 600–1000 in the San Joaquin Valley near Wasco, Calif.) during seasons when the accumulation of winter chilling hours has been marginally sufficient for those varieties.

The new grapevine variety can be distinguished from the 'Mariah' (U.S. Plant Pat. No. 9,040) variety by having different parents. It requires cane pruning for optimum productivity versus quadrilateral or single spur pruning for 'Mariah'. It exhibits less phytotoxic response to exogenous gibberellic acid applications in that it responds favorably to low levels of gibberellic acid. When grown in the Coachella Valley, the bud break of the new variety occurs seven or more days before the 'Beauty Seedless' variety rather than with the 'Beauty Seedless' variety as is the case with the 'Mariah' variety. Berries of the new variety tend to be more elongated than the 'Mariah' variety having a greater length of the longitudinal axis and a somewhat smaller diameter of the horizontal axis.

The new grapevine variety differs from the 'Larson B-36' (U.S. Plant Pat. No. 9,039) variety in having different parents. When grown in the Coachella Valley, the bud break of the new variety occurs seven or more days before the 'Beauty Seedless' variety rather than after the 'Beauty Seedless' variety as is the case with the 'Larson B-36' variety. The natural berry weight of the new variety is somewhat larger than the 'Larson B-36' variety being about 4.7 grams as opposed to 3.8 grams. The new variety appears to be less sensitive to phytotoxic effects of exogenous gibberellic acid applications.

The new grapevine variety differs from the 'Marroo' (U.S. Plant Pat. No. 7,377) variety in having different patents and is of pure vinifera species as opposed to the 'Marroo' which has the Vitis species *Berlandieri, rupestris* and *Lincecumii* in its lineage. The new variety has larger, firmer, more elongated berries with smaller less lignified vestigial seed traces compared with the 'Marroo' variety. The new variety breaks bud ten to fourteen days earlier than the 'Marroo' variety and the fruit ripens two to three weeks earlier. The new variety has a higher sugar to acid ratio than the 'Marroo' variety especially during the early stages of maturation.

The new 'Sugrathirteen' variety has been shown to maintain its distinguishing characteristics through successive asexual propagations by, for example, hardwood cuttings.

BRIEF DESCRIPTION OF THE FIGURE

The accompanying drawing in FIG. 1 illustrates, in full color, a typical cluster of berries, stem section, young shoot and mature leaf blade of the new grapevine.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published by The Royal Horitcultural Society, London, England.

Throughout this specification subjective description values conform to those set forth by the International Plant Genetic Resources Institute publication 'Descriptors for Grape' (Vitis spp.) (1983) which was developed in collaboration with the Office International de la Vigne et du Vin (OIV) and the International Union for the Protection of New Varieties of Plants (UPOV).

The descriptive matter which follows pertains to 'Sugrathirteen' plants grown in the vicinity of Wasco, Kern County, Calif. during 1995, and is believed to apply to plants of the variety grown under similar conditions of soil and climate elsewhere:

Vine

General:

*Size.*—Large.
*Vigor.*—Vigorous.
*Density of foliage.*—Medium.
*Productivity.*—Medium productive.
*Root stock.*—Own root.
*Training method.*—Typically cane pruned leaving five to seven 16-bud canes.

Trunk:

*Trunk diameter of 4-year-old vines at 30 cm above the soil line.*—8±0.89 cm.
*Shape.*—Medium.
*Straps.*—Short; split.
*Surface texture.*—Medium.
*Inner bark color.*—Greyed-orange 176D.

Shoots

Young shoot:

*Form of tip.*—Opened.
*Distribution of anthocyanin coloration of tip.*—Piping (striped).
*Intensity of anthocyanin coloration of tip.*—Absent or very weak.
*Density of prostrate hairs of tip.*—Dense.
*Density of erect hairs of tip.*—None or very sparse.

Flowering shoot:

*Vigor during flowering.*—Strong.
*Attitude during flowering on shoots not tied.*—Semi-drooping.
*Color — dorsal side of internodes.*—Yellow-green 144A.
*Color — ventral side of internodes.*—Greyed-purple 183B.
*Color — dorsal side of nodes.*—Yellow-green 144A.
*Color — ventral side of nodes.*—Yellow-green 144A.
*Density of prostrate hairs of nodes.*—None.
*Density of erect hairs of nodes.*—None.

Woody shoot (Mature canes):

*Shape.*—Medium.
*Cane length (varies greatly depending upon the vine nutrition).*—Approximately 243 cm.
*Internode length.*—About 110 mm.
*Width at node.*—About 12.4 mm.
*Cross section.*—Circular.
*Surface.*—Smooth.
*Main color.*—Reddish brown; Greyed-orange 175D.
*Lenticels.*—Absent.
*Density of erect hairs of nodes.*—None or very sparse.
*Density of erect hairs on internodes.*—None or very sparse.

Tendrils:

*Distribution on the shoot (at full flowering).*—Discontinuous.
*Length.*—About 14.5 cm.
*Thickness.*—Medium.
*Color.*—Yellow-green 145A.
*Form.*—Trifurcated.

Buds:

*Leaf producing.*—Many.
*Shape.*—Pointed.
*Size (length×width).*—About 5×6 cm.
*Bud fruitfulness.*—Basal: Unfruitful. Mid shoot and distal: Fruitful; seldom dead.
*Time of bud burst.*—Early.

Leaves

Young leaves:

*Color of upper surface.*—Yellow-green 144A.
*Average intensity of anthocyanin coloration of six distal leaves prior to flowering.*—Absent or very weak.
*Density of prostrate hairs between veins (lower surface).*—None or very sparse.
*Density of prostrate hairs on veins.*—Sparse.
*Density of erect hairs between veins (lower surface).*—None or very sparse.
*Density of erect hairs on veins.*—None or very sparse.

Mature leaves:

*Average length.*—About 10.8 cm.
*Width.*—About 16.9 cm.
*Mature leaf size.*—Medium.
*Shape of blade.*—Pentagonal.
*Number of lobes.*—5.
*Mature leaf profile.*—Involute.
*Leaf blade tip.*—In the plane of the leaf.
*Undulation of margin.*—Medium.
*Apex.*—Acuminate.
*Thickness.*—Medium.
*Undulation of blade between main and lateral veins.*—Only near petiole.
*Shape of teeth.*—Both side straight.
*Length of teeth.*—Medium.

*Shape of upper leaf sinuses.*—Lobes slightly overlapping.
*Shape of base of upper leaf sinuses.*—V-shaped.

Upper surface:
*Color.*—Green 137A.
*Anthocyanin coloration of main veins.*—Absent.
*Surface texture.*—Smooth.
*Surface appearance.*—Glossy.
*Blistering surface of blade.*—Weak.
*Goffering of blade.*—Absent.
*Density of prostrate hairs on veins.*—None or very sparse.
*Density of erect hairs on veins.*—None or very sparse.
*Autumn coloration of leaves.*—Yellow; Yellow-orange 20B; tends to retain green foliage late into the fall.

Lower surface:
*Color.*—Green 138B.
*Anthocyanin coloration of main veins (lower surface).*—Absent.
*Glossiness.*—Medium.
*Pubescence.*—Few.
*Surface texture.*—Smooth.
*Surface appearance.*—Semi-glossy.
*Density of prostrate hairs on veins.*—None or very sparse.
*Density of erect hairs on veins.*—None or very sparse.

Petiole:
*Length.*—Short; about 8.1 cm.
*Length of petiole compared to middle vein.*—Shorter.
*Density of prostrate hairs on petiole.*—None.
*Density of erect hairs on petiole.*—None.
*General shape petiole sinus.*—Open.
*Shape of base of petiole sinus.*—U-shaped.
*Particularities of petiole sinus.*—None.

Flowers

General:
*Flower sex.*—Hermaphrodite.
*Length of first inflorescence.*—Long; about 19 cm.
*Position of first flowering and fruiting node.*—5th node.
*Number of inflorescence per shoot.*—Up to 1; average= about 0.9.
*Time of bloom.*—Early as compared with similar varieties in the growing area of Wasco, Calif.
*Number borne per cane.*—About 11.4.
*Size (fully open flower).*—Medium; about 0.6 cm.

General:
*Ripening period.*—Early; about 30 days ahead of 'Thompson Seedless'.
*Use.*—Fresh market.
*Keeping quality.*—Average.
*Resistance to.*—insects: Average typical of Vitis vinifera species. diseases: Average typical of Vitis vinifera species.
*Shipping quality.*—Good.
*Date of first harvest.*—Jul. 14, 1995.
*Refractometer test.*—solid-sugar: About 16.7 Brix. acid: About 0.43 g.
*Juice pH.*—About 3.5.

Cluster:
*Size (peduncle excluded).*—Large.
*Bunch length.*—About 23.6 cm.
*Bunch width.*—About 16 cm.
*Average weight.*—About 671 g.
*Bunch density.*—Medium.
*Number of berries.*—About 147.
*Form.*—Conical.

Peduncle:
*Lignification of peduncle.*—Weak.
*Color.*—Yellow-green 145A.

Berry:
*Uniformity of size.*—Variable.
*Shape.*—Long elliptic.
*Cross section.*—Circular.
*Dimensions.*—longitudinal axis: About 26.5 mm. horizontal axis: About 18.4 mm.
*Single berry weight.*—High; about 4.7 g natural; to about 9.3 g when treated with gibberellic acid.
*Berry firmness.*—Firm.
*Bloom (cuticular wax).*—Medium.
*Berry separation from pedicel.*—Medium.
*Color.*—Black 202A.

Skin:
*Thickness.*—Average.
*Texture.*—Medium.
*Reticulation.*—Absent.
*Roughness.*—Absent.
*Flavor.*—Neutral.
*Tenacity.*—Tenacious to flesh.

I claim:

1. A new and distinct variety of grapevine cv. 'Sugrathirteen' as herein illustrated and described.

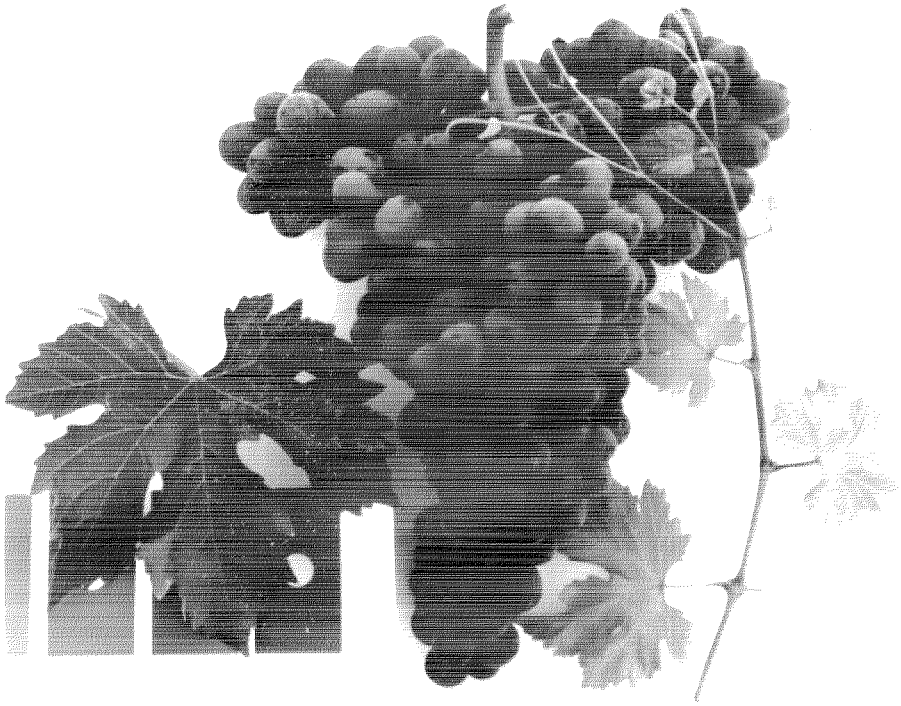
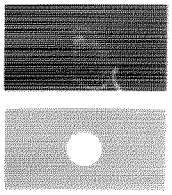

* * * * *